US012092626B2

(12) United States Patent
Mahavadi et al.

(10) Patent No.: US 12,092,626 B2
(45) Date of Patent: Sep. 17, 2024

(54) CHARACTERIZATION OF POLAR SPECIES IN RESERVOIR FLUIDS

(71) Applicant: Schlumberger Technology Corporation, Sugar Land, TX (US)

(72) Inventors: Sharath Chandra Mahavadi, Lexington, MA (US); Yi-Qiao Song, Newton Center, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 76 days.

(21) Appl. No.: 17/904,016

(22) PCT Filed: Feb. 11, 2021

(86) PCT No.: PCT/US2021/017701
§ 371 (c)(1),
(2) Date: Aug. 11, 2022

(87) PCT Pub. No.: WO2021/163359
PCT Pub. Date: Aug. 19, 2021

(65) Prior Publication Data
US 2023/0112340 A1 Apr. 13, 2023

Related U.S. Application Data

(60) Provisional application No. 62/972,670, filed on Feb. 11, 2020.

(51) Int. Cl.
*G01N 33/28* (2006.01)
*E21B 49/08* (2006.01)
(52) U.S. Cl.
CPC ....... *G01N 33/2823* (2013.01); *E21B 49/081* (2013.01)

(58) Field of Classification Search
CPC .......................... G01N 33/2823; E21B 49/081
See application file for complete search history.

(56) References Cited

U.S. PATENT DOCUMENTS 4,577,492 A * 3/1986 Holba .................... G01N 30/40
73/61.53
5,076,909 A * 12/1991 Overfield ............... C10G 21/30
585/828

(Continued)

FOREIGN PATENT DOCUMENTS

| EP | 1840567 A1 | 10/2007 |
| WO | 2016018229 A1 | 2/2016 |

OTHER PUBLICATIONS

International Preliminary Report on Patentability issued in PCT Application PCT/US2021/017701 dated Aug. 25, 2022, 7 pages.

(Continued)

*Primary Examiner* — Kristina M Deherrera
*Assistant Examiner* — Jean F Morello
(74) *Attorney, Agent, or Firm* — Jeffrey D. Frantz (57) ABSTRACT

A workflow and fluid analysis system to determine polar concentration and type of a reservoir fluid sample that is collected and analyzed in a downhole environment. Once collected this data can be fed into an advisory tool which can predict the probability of different types of issues that might be encountered in production of reservoir fluids from the reservoir. The workflow and fluid analysis system can also be employed in a surface-located laboratory tool for analysis of reservoir fluids.

17 Claims, 4 Drawing Sheets

(56) References Cited

U.S. PATENT DOCUMENTS

| | | | |
|---|---|---|---|
| 7,990,161 B2* | 8/2011 | Ju | G01N 33/2876 |
| | | | 324/459 |
| 10,718,747 B2* | 7/2020 | Pelletier | E21B 49/081 |
| 2004/0235187 A1 | 11/2004 | LaCourse et al. | |
| 2008/0149819 A1 | 6/2008 | Zhdaneev | |
| 2011/0100100 A1 | 5/2011 | Strand et al. | |
| 2012/0085645 A1 | 4/2012 | Mousa et al. | |
| 2016/0032171 A1 | 2/2016 | Barnes et al. | |
| 2017/0292375 A1* | 10/2017 | Feng | C09K 8/584 |
| 2018/0037809 A1* | 2/2018 | Frattarelli | E21B 43/20 |
| 2018/0291286 A1 | 10/2018 | Mohan et al. | |
| 2019/0316026 A1 | 10/2019 | Alvarado et al. | |
| 2020/0301039 A1 | 9/2020 | Tang et al. | |

OTHER PUBLICATIONS

ASTM D2896—Standard Test Method for Base Number of Petroleum Products by Potentiometric Perchloric Acid Titration1, West Conshohocken, PA, 2015, 10 pages.

ASTM D4739—Standard Test Method for Base Number Determination by Potentiometric Hydrochloric Acid Titration1, West Conshohocken, PA, 2017, 8 pages.

ASTM D 974—Standard Test Method for Acid and Base Number by Color-Indicator Titration1, West Conshohocken, PA, 2014, (7 pages).

ASTM D664—Standard Test Method for Acid Number of Petroleum Products by Potentiometric Titration1, West Conshohocken, PA, 2017 (11 pages).

Strassner, Effect of pH on Interfacial Films and Stability of Crude Oil-Water Emulsions, J.E. J. Pet. Tech., 1968, 20 (03), pp. 303-312.

Andersen et al., Detection and Impact of Carboxylic Acids at the Crude Oil-Water Interface, Energy Fuels 2016, 30 (6) 4475.

Andersen et al., Infrared Spectroscopic Analysis of the Composition of an Oil/Water Interfacial Film, Energy Fuels 2017, 31(9), 8959.

International Search Report and Written Opinion issued in PCT Application PCT/US2021/017701, dated May 26, 2021 (10 pages).

Extended Search Report issued in European Patent Application No. 217539717 dated Feb. 15, 2024, 7 pages.

Lashkarbolooki, M. et al., "Effect of asphaltene and resin on interfacial tension of acidic crude oil/sulfate aqueous solution: Experimental study", Fluid Phase Equilibria, 2016, 414, pp. 149-155.

* cited by examiner

CHARACTERIZATION OF POLAR SPECIES IN RESERVOIR FLUIDS

CROSS-REFERENCE TO RELATED APPLICATION

The present document is a National Stage of International Application No. PCT/US2021/017701, filed Feb. 11, 2021, which is based on and claims priority to U.S. Provisional Application Ser. No. 62/972,670, filed Feb. 11, 2020, which is are incorporated herein by reference in their entirety.

FIELD

The present application relates generally to chemical characterization of reservoir fluids.

BACKGROUND

Chemical characterization of crude oils typically involves determining the concentration of the Saturated, Aromatic, Resin, and Asphaltene fractions, which is commonly referred as the SARA characterization. The important steps in the SARA procedure are the separation and mass determination of the asphaltene fraction and separation and determination of maltene fractions viz., saturates, aromatics and resins using column chromatography. Standard methodology is accepted in the industry for this purpose which is implemented by many different service companies; although there are some differences in the exact methodology used by different parties.

However, crude oil chemistry is much more complex than SARA and precise knowledge on the molecular chemistry and functionality will be extremely useful in understanding bulk crude oil behavior and predicting potential problems with the crude oil in a given field or reservoir. Polar species in crude oil, especially the organic acid-based compounds in the crude oil, are considered to determine bulk oil properties and behavior. Such polar species can influence physical properties such as viscosity and chemical nature such as corrosivity, emulsibility, interfacial behavior etc. which are quite critical to understand for the continuous production of crude oil from a given reservoir or field.

Even though such polar species are critical for oil production, little has been done to measure them accurately in the industry. Current practice of determining polarity of crude oil involves determining Total Acid Number (TAN) per ASTM D664 and determining Total Base Number (TBN) per ASTM D2896. However, these test methods cannot provide molecular level information which is important to build better answer products to address the challenges they may pose. Furthermore, performing any of these test methods downhole or at reservoir conditions is not possible.

The total acid number (TAN) is a measurement of acidity that is determined by the amount of potassium hydroxide in milligrams that is needed to neutralize the acids in one gram of oil. It is an important quality measurement of crude oil. The TAN value indicates to the crude oil refinery the potential of corrosion problems. It is usually the naphthenic acids in the crude oil that cause corrosion problems. This type of corrosion is referred to as naphthenic acid corrosion (NAC). TAN values may also be useful in other industries where oils are used as lubricants to determine oxidation and the subsequent corrosion risk to machinery.

The TAN value of a sample can be deduced by various methods, including potentiometric titration, color indicating titration, and spectroscopic methods.

In the potentiometric titration method of measuring TAN, the sample is normally dissolved in toluene and propanol with a little water and titrated with alcoholic potassium hydroxide (if sample is acidic). A glass electrode and reference electrode is immersed in the sample and connected to a voltmeter/potentiometer. The meter reading (in millivolts) is plotted against the volume of titrant. The end point is taken at the distinct inflection of the resulting titration curve corresponding to the basic buffer solution.

In the color indicating titration method of measuring TAN, an appropriate pH color indicator, e.g. phenolphthalein, is used. Titrant is added to the sample by means of a burette. The volume of titrant used to cause a permanent color change in the sample is recorded and used to calculate the TAN value.

In the spectroscopic methods of measuring TAN, spectroscopy can be used to make fast, accurate measurements of the TAN value once calibrated by a reference method. Mid and near infrared spectroscopy are most commonly used for this purpose. Spectroscopic methods are valuable as they can also be used to simultaneously measure a number of other parameters and do away with the need for wet chemistry.

The Total Base Number (TBN) is a measurement of basicity that is expressed in terms of the equivalent number of milligrams of potassium hydroxide per gram of oil sample (mg KOH/g). TBN is an important measurement in petroleum products, and the value varies depending on its application. TBN generally ranges from 6-80 mg KOH/g in modern lubricants, 7-10 mg KOH/g for general internal combustion engine use and 10-15 mg KOH/g for diesel engine operations. TBN can be an important measurement tool to determine purity of amines as well.

The TBN value of a sample can be deduced by various methods, including potentiometric titration, color indicating titration, thermometric titration, conductometric titration, and spectroscopic methods.

In the potentiometric titration method of measuring TBN, such as TBN ASTM D2896, a sample is typically dissolved in a pre-mixed solvent of chlorobenzene and acetic acid and titrated with standardized perchloric acid in glacial acetic acid for fresh oil samples. The end point is detected using a glass electrode which is immersed in an aqueous solution containing the sample, and connected to a voltmeter/potentiometer. This causes an ion exchange in the outer solvated layer at the glass membrane, so a change in potential is generated which can be measured by the electrode. When the end point of the chemical reaction is reached, which is shown by an inflection point on the titration curve using a specified detection system, the amount of titrant required is used to generate a result which is reported in milligrams of potassium hydroxide equivalent per gram of sample (mg of KOH/g). In the potentiometric titration methods for measuring TBN of used oils, such as TBN ASTM D4739), a sample of used oil is typically dissolved in a solvent mixture of Toluene/Propan-2-ol/Chloroform with 0.5% deionized water and then titrated with standardized alcoholic hydrochloric acid. The detection system is equivalent to the fresh oil method. The used oil method uses a less polar solvent and weaker titrant, which will not dissolve the wear metals produced during operation, hence it is more suitable to analyze used oils.

In the color indicating titration methods for measuring TBN, such as ASTM D 974, a sample is dissolved in a solvent mixture of Toluene/Propan-2-ol with 0.5% deionized water. A methyl orange indicator is added, and the solution is titrated using alcoholic potassium hydroxide. The end point is indicated by a color change from orange to green under the oxidizing conditions.

In the thermometric titration methods for measuring TBN, a constant addition rate of titrant equates to a constant amount of heat being given out or consumed, and hence a more or less constant temperature changes up to the endpoint. In a titration, the titrant reacts with the analyte in the sample either exothermically or endothermically. A thermoprobe measures the temperature of the titrating solution. When all of the analyte in the sample has reacted with the titrant, the temperature of the solution will change, and the endpoint of the titration is revealed by an inflection in the temperature curve. In one example, an appropriate aliquot of the sample is pipetted directly into the titration vessel, and isobutyl vinyl ether and toluene solvent are added. The solution is then titrated with Trifluoro methane sulfonic acid (TFMSA) to a single thermometric endpoint.

Conductive titration methods can be used to measure TBN of petroleum fluids. A conductivity sensor is used to measure the conductivity of the analyte which allows the endpoint to be detected. It is suitable for both new and used products having base numbers from 1 mg to 40 mg KOH/g. A sample is typically dissolved in a solvent mixture of Toluene/Propan-2-ol with 0.5% deionized water. A conductivity cell is placed in the titration vessel. The sample solution is titrated with alcoholic hydrochloric acid.

In the spectroscopic methods of measuring TBN, mid-FTIR spectroscopy can be used to rapidly and quantitatively determine the TBN of hydrocarbon lubricating oils by spectroscopically measuring the carboxylate (COO—) functional group of the salt produced when trifluoroacetic acid (TFA) reacts with basic constituents present in an oil sample.

Polar species and their role in the interfacial activity of crude oils has been known for years. Moreover, acids are one of the more potent natural surfactants in crude oil and as such is an active component determining both emulsion stability, interfacial tension, corrosion and as an example response to alkaline injection water. All these challenges are due to interfacial film formation, which was first reported in 1960s.

Most of the studies on crude oils are focused on the role of polar species in lowering interfacial tension (IFT) of a crude oil. IFT is a property of the interface between two immiscible phases. When the phases are both liquid, it is termed interfacial tension or IFT; when one of the phases is air, it is termed surface tension. IFT occurs because a molecule near an interface has different molecular interactions than an equivalent molecule within the bulk fluid. Surfactant molecules preferentially position themselves at the interface and thereby lower the IFT.

Extensive studies have been performed on crude oil interfacial chemistry which highlighted that pH and salinity can activate the carboxylic acid species that can increase their interfacial activity, such as lowering IFT. See Strassner, J. E. J. Pet. Tech., 1968, 20, 203.

However, the role of nitrogen species in the interfacial activity of crude oil has been unclear for a long time. In Energy & Fuels 2016, 30 (6) 4475, a more recent study involved chemical analysis on the monolayer of interfacial film and determined the carboxylic acids present at the oil-water interface. Studies also revealed that significant portion of the interfacial material is non-asphaltenic. See Energy & Fuels 2017, 31(9), 8959

PCT Patent Application WO2016/018229 suggested that a Gibbs-Langmuir correction of Equation 1 can be used along with current IFT models to accurately predict the IFT.

$$\gamma - \gamma_0 = -RTT_m \ln(1 + K_L C) \quad \text{Eq. (1)}$$

Similar models can be developed for other production issues such as emulsion stability, corrosion, scaling etc. that rely on characterizing acid or polar concentration.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In embodiments of the subject disclosure, a workflow and fluid analysis system is provided to determine polar concentration and type of a reservoir fluid sample that is collected and analyzed in a downhole environment (e.g., as part of a downhole tool that is located in a wellbore that traverses a subterranean reservoir). Once collected this data can be fed into an advisory tool which can predict the probability of different types of issues that might be encountered in production of reservoir fluids from the reservoir. The workflow and fluid analysis system can also be employed in a surface-located laboratory tool for analysis of reservoir fluids.

The workflow and fluid analysis system is concerned with the determination of the presence of natural surfactants and their polarity gradient. The workflow and fluid analysis system includes an experimental part and a data interpretation part. The experimental part collects and analyzes a reservoir fluid sample to determine polar concentration and type of the reservoir fluid sample. The data interpretation part processes the result data produced by the experimental part to predict the probability of different types of issues that might be encountered in production of reservoir fluid. In embodiments, the data interpretation part can be an advisory tool that processes the result data either through simple analysis or ML (Machine learning) based algorithms to predict the probability and gradient of different types of production issues, such as emulsion stability, interfacial tension, organic scaling, corrosion and water floods for EOR applications, etc. Most of these properties or issues are associated with the presence of polar species (acidic and basic species). In one or more embodiments, polar species concentration of at least 0.0001 weight percent can trigger any of these issues. In one more embodiments, a polar species concentration less than 0.0001 weight percent can trigger any of these issues.

Further features and advantages of the subject application will become more readily apparent from the following detailed description when taken in conjunction with the accompanying drawings.

BRIEF DESCRIPTION OF THE DRAWINGS

The present application is further described in the detailed description which follows, and in reference to the noted plurality of drawings by way of non-limiting examples of embodiments of the present application, in which like reference numerals represent similar parts throughout the several views of the drawings.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

In accordance with the present disclosure, a workflow and fluid analysis system is provided to determine polar concentration and type of a reservoir fluid sample (e.g., crude oil or a mixture of oil and connate water or connate water alone or crude oil, connate water, and other previously introduced chemicals or material, or mixtures thereof). In embodiments, the determination of the polar concentration of the sample is performed in two steps. In the first step, the polar species of the sample is removed by passing the sample through one or more cartridges. In embodiments, the cartridge(s) can be a tube that is filled with tailored particle material or materials viz., ion exchange resin (cationic or anionic), rock materials such as silica, sandstone, carbonate or any other rock material or adsorbent to remove selective species (such as acids or amines) from the sample as the sample passes through the tube. Also, multiple cartridges can be prepared by packing with more than one type of material in series. Such particles can be further coated with materials to selectively adsorb certain polar species. The size of the adsorbent particles loaded into the cartridge(s) can be tuned from nano- to millimeter sizes and/or the length of the cartridge(s) can be tuned within a wide range of lengths, with a preferred length between 1 cm to 10 cm. The packing density of the cartridge(s) can also be varied either by particle size or pressure or any other means.

Once the sample is passed through the cartridge(s), the cartridge(s) can be washed with other fluid (e.g., liquid and/or gas), such as compressed air or a gas phase solvent, to clear those molecules that are not tightly bound to the particle surfaces, for example, trapped oils.

Then, the polar species of the sample can be detected on the surface of the cartridge packing material. For example, the cartridge may be directly used in an NMR measurement to determine the amount of polar species on the particle surfaces without removing them. The polar species can also be detected by releasing the adsorbed material from the particle surface. This can be achieved by flushing with liquid or gaseous solvents and the resulting samples can be analyzed with a sensor (such as NMR, optical spectroscopy or electrochemical sensors or other suitable fluid sensor).

Additionally, the part of the sample that has passed through the cartridge (with the polar species removed), namely the non-polar part of the sample, can be analyzed with a sensor and compared with analytical results of the sample (before extraction of the polar species of the sample) to provide an estimate of the polar species. The analysis can be performed using one or more sensors (such as an NMR sensor, optical spectrometer or electrochemical sensor or other suitable sensor).

Note that by varying the packing type in the cartridge(s), the workflow and fluid analysis system can selectively separate different types of polar and non-polar species (such as acids, amines, resins, aromatics, saturates, and in some cases asphaltenes) from the sample.

Furthermore, the cartridges can be prepared with different reservoir rock materials to better understand how the sample behaves when it is exposed to different rock material in a given formation or reservoir.

The workflow can be carried out under high pressure/high temperature conditions in a downhole environment as part of a downhole tool that is located in a wellbore that traverses a subterranean reservoir. Alternatively or additionally, the workflow can be performed under high pressure/high temperature conditions in the surfaced-located laboratory set up. For example, high temperature high pressure NMR systems can be used to perform such measurement in a downhole tool or in a lab.

The workflow can be performed in multiple zones in a given oil well or multiple wells in a given field or multiple fields connected to a reservoir in order to build polarity data (referred to as a 'Polarity Scale') which will help in adopting different prevention and/or mitigation strategies for potential issues. This polarity scale readings can also be used as an input in Eqn. 1 instead of actual concentration of polar species.

Figure 1:
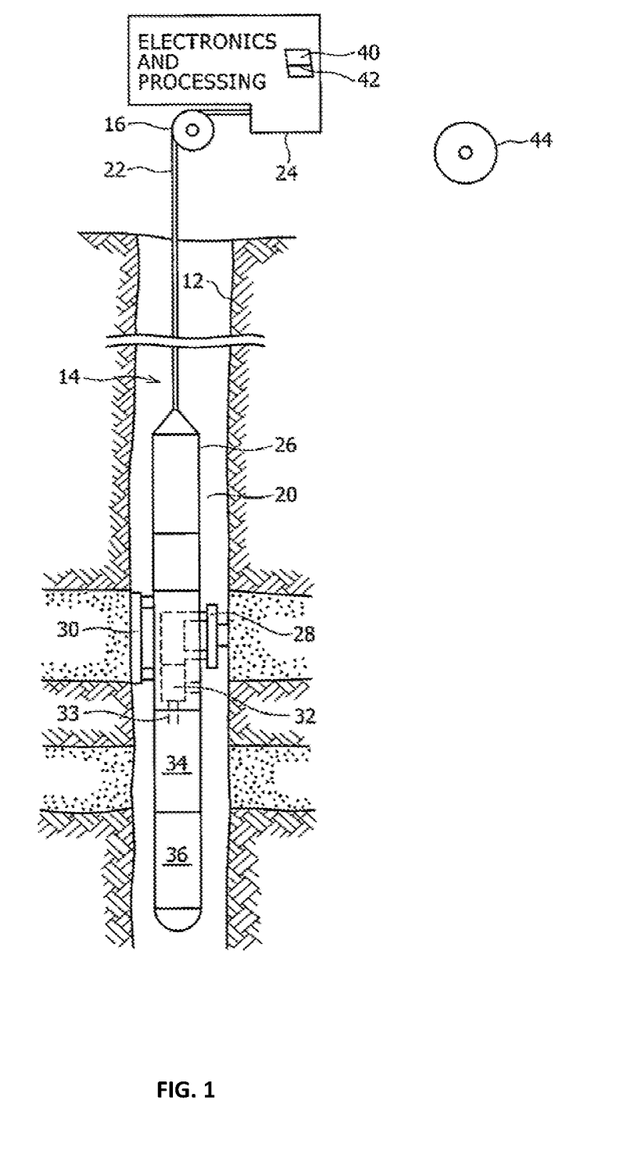
FIG. 1 is a schematic diagram of a system for downhole analysis of reservoir fluids.

FIG. 1 is a schematic diagram that illustrate an embodiment of a system 14 for downhole analysis of reservoir fluids according to the present disclosure. The system 14 includes a tool string 20, which may be used for testing earth formations and analyzing the composition of fluids from a formation. The tool string 20 typically is suspended in a borehole 12 from the lower end of a multiconductor logging cable or wireline 22 spooled on a winch 16 at the formation surface. The wireline 22 is typically electrically coupled to a surface electrical control system 24 having appropriate electronics and processing systems for the tool string 20.

The tool string 20 includes an elongated tool body 26 encasing a variety of electronic components and modules. A fluid admitting assembly 28 and tool-anchoring member 30 are respectively arranged on opposite sides of the elongated tool body 26. The fluid admitting assembly 28 is operable for selectively sealing off or isolating selected portions of a borehole 12 such that pressure or fluid communication with adjacent earth formation is established. One or more fluid analysis modules 32 are provided in the elongated tool body 26. Fluids obtained from a formation and/or borehole flow through a flowline 33, via the one or more fluid analysis of modules 32, and then may be discharged through a port of a pump out module. Alternatively, formation fluids in the flowline 33 may be directed to one or more fluid collecting chambers 34 and 36 for receiving and retaining the fluids obtained from the formation for transportation to the surface.

Figure 2:
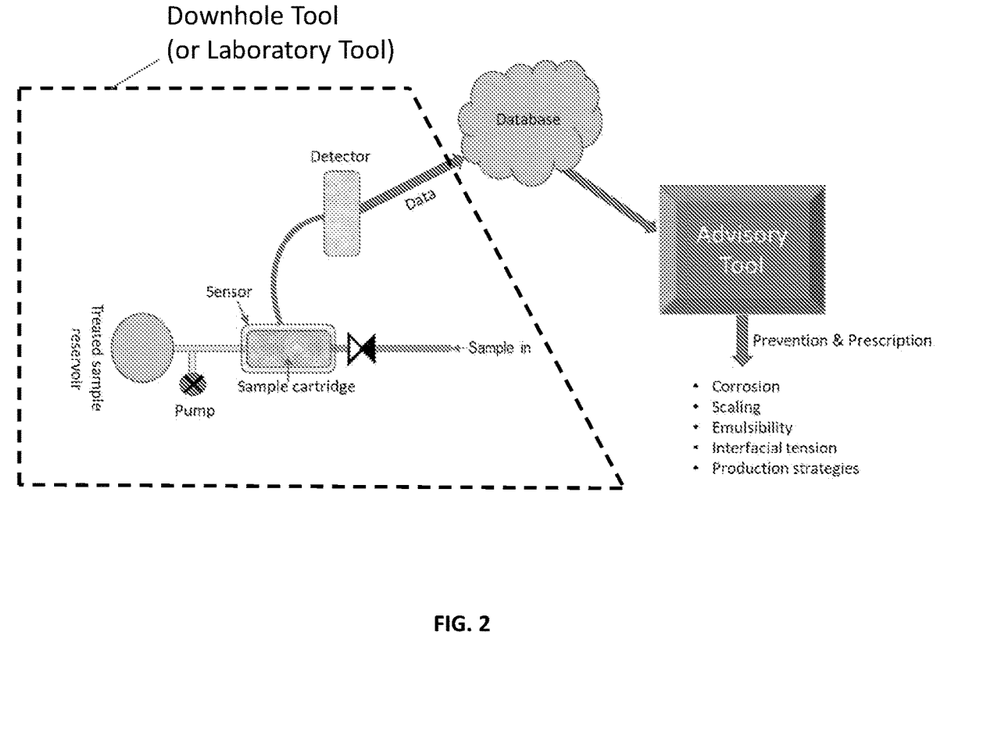
FIG. 2 is a schematic diagram of downhole tool that is configured to carry out a workflow that determines polar concentration and type of a reservoir fluid sample.

The fluid admitting assembly, fluid analysis module(s), the flow path and the collecting chambers, and other operational elements of the tool string 20 can be controlled by electrical control systems, such as the surface electrical control system 24 (note FIG. 2). Preferably, the surface electrical control system 24, and other control systems situated in the elongated tool body 26, for example, include processor capability for characterization of formation fluids as described in more detail below.

The system 14 preferably includes a control processor 40 operatively coupled to the tool string 20. The control processor 40 is depicted in FIG. 1 as an element of the surface electrical control system 24. Preferably, certain parts of the workflow as described herein can be embodied in a computer program that runs in the control processor 40 located, for example, in the surface electrical control system 24. In operation, the program is coupled to receive data, for example, from the one or more fluid analysis module(s) 32, via the wireline 22, and to transmit control signals to operative elements of the tool string 20.

The computer program may be stored on a computer usable storage medium 42 associated with the control processor 40 or may be stored on an external computer usable storage medium 44 and electronically coupled to control processor 40 for use as needed. The storage medium 44 may be any one or more of presently known storage media, such as a magnetic disk fitting into a disk drive, or an optically readable CD-ROM, or a readable device of any other kind, including a remote storage device coupled over a switched telecommunication link, or future storage media suitable for the purposes and objectives described herein.

In other embodiments, the tool string 20 can be conveyed by drill pipe or tubing or other conveyance mechanism as part of a logging—while drilling tool or other downhole tool.

FIG. 2 is a schematic diagram of a downhole tool (e.g., part of the tool string 20 of FIG. 1) that is configured to carry out operations of the workflow as described herein. In this embodiment, the downhole tool is configured to inject a reservoir fluid sample (e.g., crude oil) at high pressure high temperature conditions of the downhole environment (labeled "sample in") into a sample cartridge. While the sample flows through the cartridge, selected polar species will be adsorbed onto it and the treated sample (effluent) will be sent to the reservoir at the end of the line. Excess reservoir fluid can be sneezed out from the column using the pump.

The material adsorbed by the cartridge will be detected by a sensor (such as NMR, optical spectroscopy or electrochemical sensors or other suitable sensor).

While the sample is flowing into the system prior to entering the cartridge and after leaving the cartridge, the same sensor (or some other sensor) can be used to measure physical properties of the fluid, such as viscosity and density as well as chemical properties which is not limited to composition of the sample and change after the treatment.

Data generated by the sensor(s) can be incorporated into cloud database or local database. Such data will be supplied to an advisory tool which can provide probability of various issues with that sample and potential strategies to increase the longevity of the producing well.

This analysis can be performed in multiple zones in the well or multiple wells in a field or multiple fields in a given reservoir to understand potential challenges and develop right strategies for production.

Figure 3:
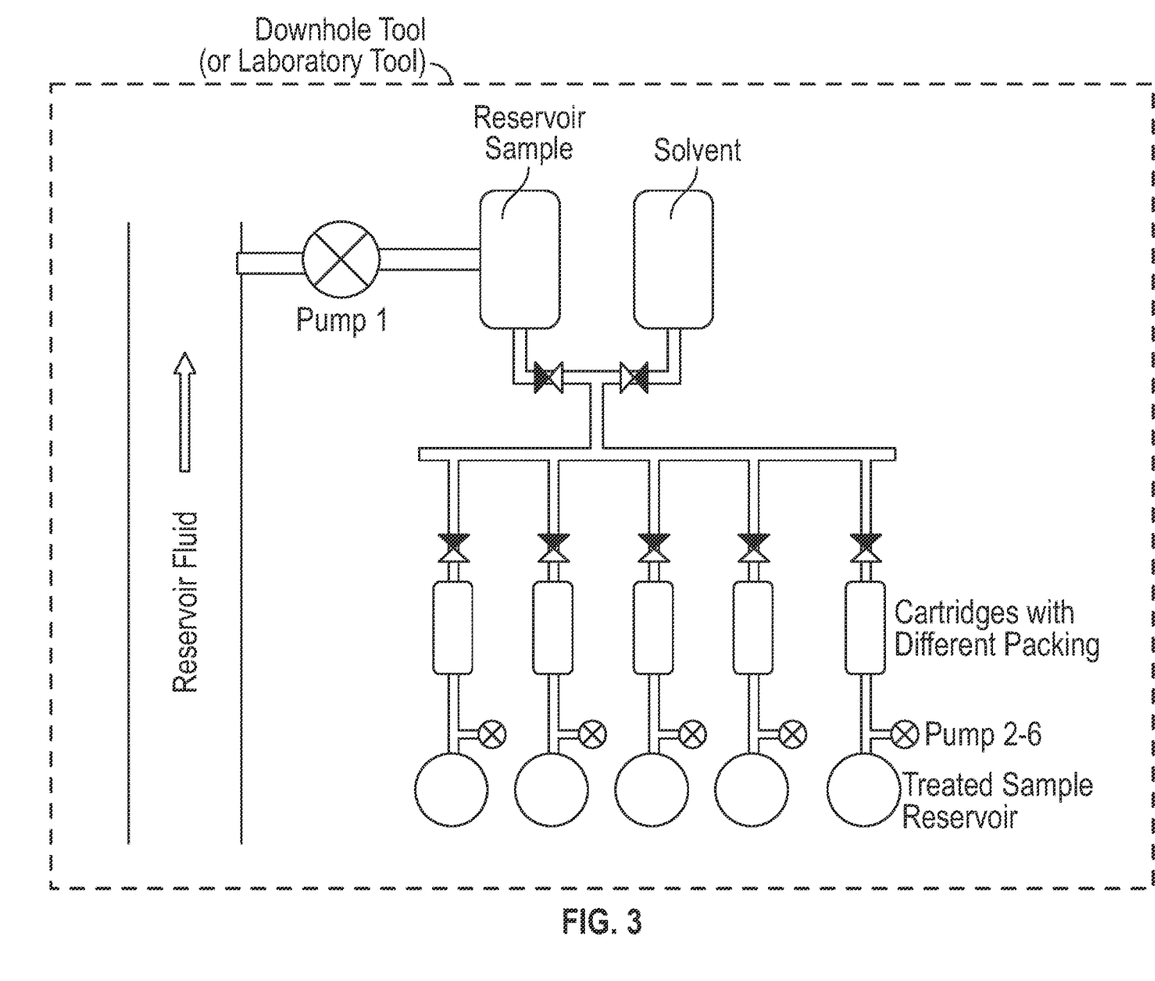
FIG. 3 is a schematic diagram of another downhole tool that is configured to carry out a workflow that determines polar concentration and type of a reservoir fluid sample.

FIG. 3 is a schematic diagram of a downhole tool (e.g., part of the tool string 20 of FIG. 1) which houses different types of cartridges that are configured to perform selective separation of the sample and perform multiple analysis at the same time. There can be multiple units configured to perform similar analysis in multiple zones in a given well, etc.

The cartridges presented in FIG. 3 can also be connected in series in order to extract from the same crude oil or any other sample.

In alternate embodiments, similar measurements can be carried out at high pressure high temperature conditions or ambient conditions as part of a surface-located laboratory tool, such as a laboratory NMR tool, optical spectrometer or other suitable tool.

The following presents a specific example with NMR, where polar species are separated from a crude oil sample onto a special cartridge material and then analyzed with NMR spectroscopy.

Figure 4:
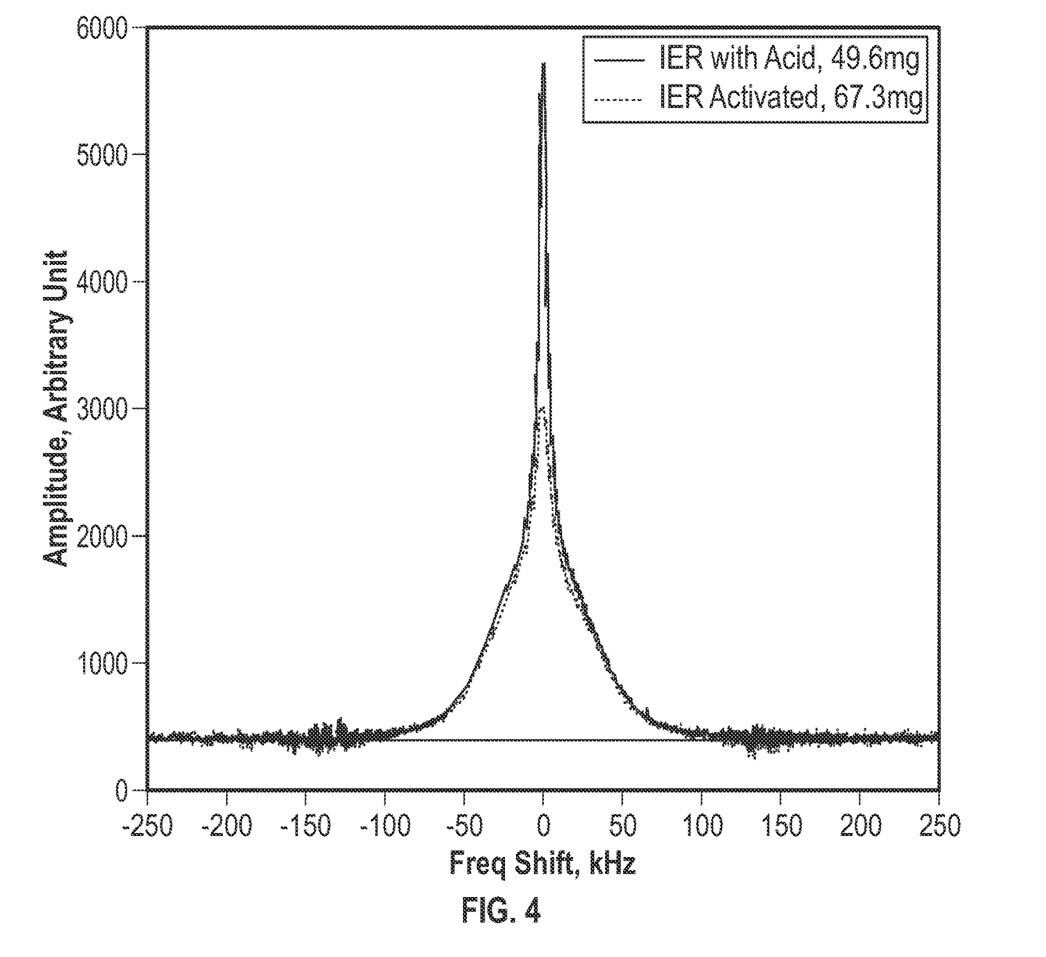
FIG. 4 depicts plots that show NMR spectra analysis of polar species of a crude oil sample adsorbed onto a cartridge in accordance with the workflows and systems of the present disclosure.

An FID experiment was performed on two ion exchange resin (IER) cartridges and the frequency spectra are shown in FIG. 4. The frequency spectrum is obtained by Fourier transform of the time domain data acquired by the FID experiment. One cartridge employs activated IER particles before being exposed to the crude oil. The second cartridge employs IER particles with adsorbed acid molecules. This second cartridge is prepared by stirring a crude oil sample for 12 hours with the IER material. After 12 hours, the IER with acid sample was cleaned to remove the excess oil so that only the strongly adsorbed molecules are on the surface of the particles. Here the IER is representative of the cartridge packing material, which will perform similar activity of separating different chemical species selectively.

FIG. 4 depicts plots that show NMR spectra analysis of polar species of a crude oil sample adsorbed onto a cartridge. The blue line (IER activated) is the NMR spectrum signal from the first cartridge before exposure to the crude oil sample. The red line (IER with acid) is the NMR spectrum signal from the second cartridge exposed to the crude oil. The spectra are normalized by the weight of the sample. The additional amplitude in the red line signal is indicative of the adsorbed molecules on the particles in the second cartridge. This additional signal can be obtained by subtracting IER active signal from the IEA acid signal. This difference signal can be calibrated to determine the amount of the adsorbed molecules.

In addition to the FID experiment, other NMR experimental techniques can be used too. For example, CPMG, solid echo, magic echo experimental techniques can be used to determine the relaxation time of the adsorbed molecules. Multi-dimensional NMR spectroscopy can also be used to determine the molecular species of the sample.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively, or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

The components, steps, features, objects, benefits and advantages that have been disclosed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

In the present application, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of analyzing a reservoir fluid sample, the method comprising: passing the reservoir fluid sample through at least one cartridge, wherein the at least one cartridge is configured to adsorb at least one polar species of the reservoir fluid sample; and using at least one sensor to: analyze the adsorbed at least one polar species; and generate data characterizing a type and a concentration of the at least one polar species of the reservoir fluid sample:
wherein the at least one polar species is selected from acidic and basic species.

2. The method according to claim 1, further comprising using a fluid to flush the at least one polar species from the at least one cartridge, wherein using the at least one sensor to generate the data characterizing the at least one polar species of the reservoir fluid sample includes analyzing the fluid flushed from the at least one cartridge in order to generate the data characterizing the at least one polar species of the reservoir fluid sample.

3. The method according to claim 1, further comprising using the at least one sensor or an additional sensor to generate additional data characterizing properties of the reservoir fluid sample before the reservoir fluid sample is injected into the at least one cartridge, wherein generating the data characterizing the type and the concentration of the at least one polar species is based on the analysis of the adsorbed at least one polar species and the additional data.

4. The method according to claim 1, further comprising using the at least one sensor or an additional sensor to generate additional data characterizing at least one of physical properties or chemical properties of the reservoir fluid sample that has passed through the at least one cartridge.

5. The method according to claim 4, wherein the physical properties of the reservoir fluid comprises at least one of: a viscosity, a density, or a composition of the reservoir fluid sample.

6. The method according to claim 1, further comprising:
inputting the data characterizing the at least one polar species of the reservoir fluid sample to an advisory tool; and
predicting, with the advisory tool, potential production issues based on the data characterizing the at least one polar species of the reservoir fluid sample.

7. The method according to claim 1, further comprising collecting the reservoir fluid sample at high pressure high temperature downhole conditions, wherein passing the reservoir fluid sample through the least one cartridge includes passing the reservoir fluid sample through the at least one cartridge at the high pressure high temperature downhole conditions.

8. The method according to claim 1, wherein the reservoir fluid sample is passed through the at least one cartridge at ambient conditions.

9. The method according to claim 1, wherein the at least one sensor comprises a nuclear magnetic resonance (NMR) sensor, an optical spectrometer, or an electrochemical sensor.

10. The method according to claim 1, wherein the at least one cartridge is filled with material that is configured to adsorb the at least one polar species of the reservoir fluid sample.

11. The method according to claim 1, wherein the at least one cartridge comprises a plurality of cartridges filled with different materials that are configured to adsorb different polar species of the reservoir fluid sample.

12. The method according to claim 1, wherein the at least one cartridge comprises a plurality of cartridges filled with different types of rock material.

13. The method according to claim 1, further comprising:
repeating the method for multiple zones in a well, for multiple wells in a field, or for multiple fields connected to a reservoir;
building polarity data based on data generated repeating the method; and
using the polarity data to adopt at least one of different prevention strategies or mitigation strategies for potential production issues associated with the multiple zones, the multiple wells, or the multiple fields.

14. A tool comprising: a cartridge operatively in communication with a flowline of the tool, wherein the cartridge is configured to adsorb a selected polar species of a fluid communicated to the cartridge; and a detector operatively configured to detect a type and a concentration of the selected polar species adsorbed on the cartridge;

wherein the polar species is selected from acidic and basic species.

15. The tool of claim 14, wherein the tool is a laboratory tool or a downhole tool.

16. The tool of claim 14, wherein the tool comprises a plurality of cartridges.

17. The tool of claim 16, wherein each cartridge of the plurality of cartridges are configured to adsorb a different selected polar species.

\* \* \* \* \*